(12) United States Patent
Chatterjea et al.

(10) Patent No.: US 12,111,323 B2
(45) Date of Patent: Oct. 8, 2024

(54) CLASSIFICATION OF PERIODONTITIS PATIENTS

(71) Applicant: KONINKLIJKE PHILIPS N.V., Eindhoven (NL)

(72) Inventors: Supriyo Chatterjea, Eindhoven (NL); Marinus Karel Johannes De Jager, Eindhoven (NL); Amir Hussein Rmaile, Eindhoven (NL); Gerben Kooijman, Leende (NL); Michael Alex Van Hartskamp, Eindhoven (NL); Philip Preshaw, Newcastle upon Tyne (GB); John J Taylor, Framlington Place (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1197 days.

(21) Appl. No.: 16/758,902

(22) PCT Filed: Oct. 18, 2018

(86) PCT No.: PCT/EP2018/078486
§ 371 (c)(1),
(2) Date: Apr. 24, 2020

(87) PCT Pub. No.: WO2019/086252
PCT Pub. Date: May 9, 2019

(65) Prior Publication Data
US 2021/0181209 A1   Jun. 17, 2021

(30) Foreign Application Priority Data
Oct. 30, 2017 (EP) ..................................... 17199175

(51) Int. Cl.
G01N 33/68   (2006.01)

(52) U.S. Cl.
CPC . *G01N 33/6893* (2013.01); *G01N 2333/4753* (2013.01); *G01N 2333/5412* (2013.01); *G01N 2333/545* (2013.01); *G01N 2333/78* (2013.01); *G01N 2333/8146* (2013.01); *G01N 2333/96494* (2013.01); *G01N 2800/18* (2013.01)

(58) Field of Classification Search
None
See application file for complete search history.

(56) References Cited

U.S. PATENT DOCUMENTS

| | | | |
|---|---|---|---|
| 5,516,699 A | 5/1996 | Giannobile et al. | |
| 2008/0027146 A1 | 1/2008 | Fiorellini et al. | |
| 2010/0196941 A1* | 8/2010 | Braun ............... | G01N 33/6893 435/23 |
| 2015/0219665 A1 | 8/2015 | Chapple et al. | |
| 2015/0301063 A1 | 10/2015 | Alman et al. | |

FOREIGN PATENT DOCUMENTS

| | | |
|---|---|---|
| WO | 9405806 A1 | 3/1994 |
| WO | 2009018342 A1 | 2/2009 |
| WO | 2010040097 A1 | 4/2010 |
| WO | 2015117881 A1 | 8/2015 |
| WO | 2017149206 A1 | 9/2017 |

OTHER PUBLICATIONS

AlRowis R, AlMoharib HS, AlMubarak A, Bhaskardoss J, Preethanath RS, Anil S. Oral fluid-based biomarkers in periodontal disease—part 2. Gingival crevicular fluid. J Int Oral Health. Sep. 2014;6(5):126-35. (Year: 2014).*
Taylor JJ. Protein biomarkers of periodontitis in saliva. ISRN Inflamm. Apr. 22, 2014;2014:593151. (Year: 2014).*
Nicolaos Christodoulides et al. "Lab-on-a-Chip Methods for Point-of-Care Measurements of Salivary Biomarkers of Periodontitis". Annals of the New York Academy of Sciences. vol. 1098, Issue 1, pp. 411-428. Apr. 2, 2007.
Suk Ji et al. "Point-of-Care Diagnosis of Periodontitis Using Saliva: Technically Feasible for Still a Challenge". Frontiers in Cellular and Infection Microbiology, vol. 5, Issue 65, pp. 1-9. Sep. 3, 2015.
International Search Report and Written Opinion, International Application PCT/EP2018/078486, Mailed on Nov. 21, 2018.
Korte, D. et al., "Personalized medicine: an update of salivary biomarkers for periodontal diseases", Periodontology 2000, vol. 70, No. 1.
Kinney, J. et al., "Saliva/Pathogen Biomarker Signatures and Periodontal Disease Progression", Journal of Dental Research, vol. 90, No. 6, Jun. 2011.
Kakimoto, K. et al., "Hepatocyte growth factor in gingival crevicular fluid and the distribution of hepatocyte growth factor-activator in gingival tissue from adult periodontitis", Archives of Oral Biology, vol. 47, No. 9, Sep. 1, 2002.
Ji, S. et al., "Point-of-care diagnosis of periodontitis using saliva: technically feasible but still a challenge", Frontiers in Cellular and Infection Microbiology, vol. 5, Sep. 3, 2015.
Morgan, R. G., "Quality evaluation of clinical records of a group of general dental practitioners entering a quality assurance programme", British Dental Journal, vol. 191, No. 8, Oct. 27, 2001.

(Continued)

*Primary Examiner* — John S Brusca
*Assistant Examiner* — Jonathan Edward Hayes (57) ABSTRACT

Disclosed is a system, a kit, a use and an in vitro method for assessing whether a human patient suffering from periodontitis has mild periodontitis or advanced periodontitis. The system and method are based on the insight to apply a clustering technique to a reference set of patient data, and then further discriminating the sets of bio markers to be applied. The clusters are determined on the basis of the biomarkers Hepatocyte Growth Factor (HGF), Matrix metalloproteinase 8 (MMP8), and Matrix metalloproteinase 9 (MMP9). The actual classification of the patient is done on the basis of the measurement of the concentrations of either of two sets of biomarkers. For one cluster these are Interleukin-1β (IL1β), Interleukin-6 (IL6), and Collagen Telopeptide. For the other cluster, these are HGF and metallopeptidase inhibitor 1 (TIMP1).

17 Claims, 2 Drawing Sheets

(56) References Cited

OTHER PUBLICATIONS

"The Siolhouette Coefficient", Cluster Analysis: Basic Concepts and Algorithms, https://cs.fit.edu/~pkc/classes/ml-internet/silhouette.pdf, Accessed Apr. 22, 2020.

Burt BA. (2005) "Concepts of risk in dental public health", Comm Dent Oral Epi 33:240-247.

Papapanou PN. (1999) "Current and Future Approaches for Diagnosis of Periodontal Diseases", J Int Acad Perio 1:110-116.

Bartova, J. et al., "Periodontitis as a Risk Factor of Atherosclerosis," Journal of Immunology Research, vol. 2014, Article ID 636893, 9 pages, 2014. doi:10.1155/2014/63689.

Lockhart et al; Periodontal disease and atherosclerotic vascular disease: does the evidence support an independent association? A scientific statement from the American Heart Association. Circulation 2012;125(20):2520-2544.

Koromantzos et al (2012) Effect of non-surgical periodontal therapy on C-reactive protein, oxidative stress, and matrix metalloproteinase (MMP)-9 and MMP-2 levels in patients with type 2 diabetes: a randomized controlled study. Journal of Periodontology 83, 3-1.

Madianos et al Adverse pregnancy outcomes (APOs) and periodontal disease: pathogenic mechanisms. J. Periodontol., 84 (2013), pp. S170-S180 http:/dx.doi.org/10.1902/jop.2013.1340015.

Pischon et al. Association among rheumatoid arthritis, oral hygiene, and periodontitis. J Periodontol 2008, 79:979-986.

Friedrich et al. Inverse association between periodontitis and respiratory allergies. Clin Exp Allergy, 36 (2006), pp. 495-502.

Morgan, R., "Quality evaluation of clinical records of a group of general dental practitioners entering a quality assurance programme", Brit Dent J 191: 436-41, Oct. 2001.

Lee et al. Salivary diagnostics. Orthod Craniofac Res, 12 (3) (2009), pp. 206-211.

Kim et al. Salivary biomarkers in the diagnosis of periodontal diseases. J Calif Dent Assoc. 2013;41(2):119-124.

Giannobile WV: Salivary diagnostics for periodontal diseases. J Am Dent Assoc 2012, 143:6S-11S.

\* cited by examiner

CLASSIFICATION OF PERIODONTITIS PATIENTS

This application is the U.S. National Phase application under 35 U.S.C. § 371 of International Application No. PCT/EP2018/078486, filed on 18 Oct. 2018, which claims the benefit of European Application Serial No. 17199175.5, filed 30 Oct. 2017. These applications are hereby incorporated by reference herein.

FIELD OF THE INVENTION

The invention is in the field of oral care, and pertains to diagnostics of periodontal disease based on biomarkers in oral fluid, such as saliva. Particularly, the invention pertains to a kit, system, use and methods for classifying periodontitis patients as having mild or advanced periodontitis.

BACKGROUND OF THE INVENTION

Periodontitis is a chronic multifactorial inflammatory disease caused by oral microorganisms and characterized by progressive destruction of the hard (bone) and soft (periodontal ligament) tissues, ultimately leading to tooth mobility and loss. This is to be distinguished from gingivitis which is a reversible infection and inflammation of the gum tissues. Inflammatory periodontitis is one of the most prevalent chronic human diseases and a major cause of adult tooth loss. In addition to the substantial negative impact of periodontitis on oral health, there is also mounting evidence that periodontitis has systemic consequences and that it is a risk factor for several systemic diseases, including heart diseases (e.g. atherosclerosis, stroke), diabetes, pregnancy complications, rheumatoid arthritis and respiratory infections.

Early and accurate diagnosis of periodontal disease, thus, is important from both an oral and overall health perspective.

Periodontal diseases are still poorly diagnosed in general dental practice (Morgan R G (2001). Brit Dent J 191: 436-41), resulting in relatively low rates of therapeutic intervention and significant amounts of untreated cases. Current diagnosis relies on imprecise, subjective clinical examination of oral tissue condition (colour, swelling, extent of bleeding on probing, probing pocket depth; and bone loss from oral x-rays) by dental professionals. These conventional methods are time consuming, and some of the techniques used (pocket-depth, x-ray) reflect historic events, such as past disease activity, rather than current disease activity or susceptibility to further disease. Hence, more objective, faster, accurate, easier-to-use diagnostics which preferably may also be performed by non-specialists are desirable. Thereby it is desirable to measure current disease activity, and possibly a subject's susceptibility to further periodontal disease.

Saliva or oral fluids have long been advocated as a diagnostic fluid for oral and general diseases, and with the advent of miniaturized bio sensors, also referred to as lab-on-a-chip, point of care diagnostics for rapid chair-side testing have gained greater scientific and clinical interest Especially for periodontal disease detection, inflammatory biomarkers associated with tissue inflammation and breakdown may easily end up in saliva due to proximity, suggesting saliva has strong potential for periodontal disease detection. Indeed, this area thus has gained significant interest and encouraging results have been presented, yet no definite test has emerged yet.

Biomarkers represent biological indicators that underpin clinical manifestations, and as such are objective measures by which to diagnose clinical outcomes of periodontal disease. Ultimately, proven biomarkers could be utilized to assess risk for future disease, to identify disease at the very earliest stages, to identify response to initial therapy, and to allow implementation of preventive strategies.

Previous limitations to the development of point-of-care tests for salivary biomarkers included a lack of technologies that were adaptable to chair-side applications and an inability to analyse multiple biomarkers in individual samples. Also the selection of which multiple biomarkers to include in such a test has not been adequately addressed in the literature nor implemented in practical tests.

Moreover, periodontitis can manifest itself across the entire spectrum of severity ranging from mild and mild-moderate to advanced forms of the disease. In order to easily assess the severity of the condition, dentists often classify patients suffering from periodontitis into two groups—those suffering from mild periodontitis (including moderate periodontitis), and those suffering from advanced periodontitis. The available methods of making such an assessment, however, involve a labour intensive process that a dentist will not perform routinely on every patient and/or on every visit, and that is impossible to perform by a consumer (self-diagnosis).

It would be desired to provide a simpler process, and particularly a process that requires only that a small saliva sample is taken from a patient, and possibly by the patient him- or herself. It is desired that such a sample be entered into an in vitro diagnostic device, which will allow, based on measurement, a classification of the saliva sample such that it can return an indication of the likelihood that the patient is to be classified as suffering from mild periodontitis or as suffering from advanced periodontitis. A particular challenge in finding an in vitro assay on the basis of biomarkers, is to find, despite an inherent non-homogeneity of patient populations, a still limited set of biomarkers allowing to provide a desirable diagnostic sensitivity and specificity.

SUMMARY OF THE INVENTION

In order to better address the foregoing desires, the invention, in one aspect, concerns a system for classifying a human subject as having mild periodontitis or advanced periodontitis, the system comprising:
  detection means configured to measure in a sample of oral fluid of the subject the concentrations of the biomarkers Hepatocyte Growth Factor (HGF), Matrix metalloproteinase 8 (MMP8), Matrix metalloproteinase 9 (MMP9), Interleukin-113 (IL113), Interleukin-6 (IL6), Collagen Telopeptide, and, optionally, metallopeptidase inhibitor 1 (TIMP1);
  one or more processing units configured to determine a classification result from the measured concentrations of biomarkers in an oral fluid sample of the subject;
  wherein the system is configured to measure, in a first stage, the concentrations of a set of biomarkers comprising HGF, MMP8, and MMP9 so as to obtain a measurement result of first-stage concentrations, and wherein a processing unit is configured to process said first-stage concentrations such as to present a result whether or not to measure, in a second stage, the concentrations of a set of biomarkers comprising IL1-13, IL6, and Collagen Telopeptide, whereby said processing unit is optionally configured to process said first-stage concentrations such as to alternatively indicate to measure, in a second stage, the concentration of TIMP1, wherein the system is configured to obtain a measurement result of second-stage concentrations, and whereby a processing unit is configured to process the second-stage concentrations such as to present a classification result of mild or advanced periodontitis.

The system optionally contains a data connection allowing results obtained from the one or more processing units to be directed to an interface, particularly a graphical user interface, capable of presenting information, said interface being either a part of the system or a remote interface.

Optionally one or more of the foregoing items, particularly the processor, are enabled to function "in the cloud", i.e., not on a fixed machine, but by means of an internet-based application.

In another aspect, the invention presents an in vitro method for assessing whether a human subject, suspected to have periodontitis, has mild periodontitis or advanced periodontitis, wherein the method comprises measuring in a sample of oral fluid from said subject, the concentrations of the proteins HGF, MMP8, and MMP9:

comparing the measurement results with cluster centres obtained by (i) determining the concentrations of the proteins HGF, MMP8, and MMP9 in oral fluid samples of a group of patients known to have periodontitis; (ii) subjecting the results obtained for said patients to a clustering technique so as to obtain two clusters, viz. a first defined cluster and a second non-defined cluster, so as to determine whether the measurement results for the subject fit with the first or the second cluster;

in the event of a subject fitting with the first cluster, subjecting a sample of oral fluid of said subject to a further measuring of protein concentrations, said proteins comprising IL1-β, IL6, and Collagen Telopeptide, thereby obtaining a testing value reflecting the joint concentrations measured for said proteins;

in the event of a subject fitting with the second cluster, optionally subjecting a sample of oral fluid of said subject to further measuring of the concentration of TIMP1, thereby obtaining a testing value reflecting the joint concentrations measured for said TIMP1 and the earlier measured concentration of HGF;

comparing the testing value obtained with a threshold value reflecting in the same manner the joint concentrations associated with advanced periodontitis, so as to assess whether the results are indicative for mild periodontitis or for advanced periodontitis in said subject.

In a still further aspect, the invention provides a kit for determining the concentration of biomarkers for periodontitis in oral fluid, said kit comprising seven detection reagents, each detection reagent directed to a different biomarker, wherein the detection reagents are capable of binding, respectively, HGF, MMP8, MMP9, IL1-β, IL6, Collagen Telopeptide, and TIMP1, and wherein the kit is configured to as to separately process the concentrations of three different sets of said biomarkers, viz. a first set comprising HGF, MMP8, and MMP9, a second set comprising IL1-β, IL6, and Collagen Telopeptide, and a third set comprising TIMP1 and HGF.

In a yet further aspect, the invention provides a method of diagnosing whether a human patient suspected of having periodontitis has mild periodontitis or advanced periodontitis, on the basis of the concentrations of proteins in a sample of oral fluid from the patient, the method comprising:

measuring in a sample of oral fluid of the human patient the concentrations of the proteins HGF, MMP8, and MMP9;

comparing the measurement results with cluster centres obtained by (i) determining the concentrations of the proteins HGF, MMP8, and MMP9 in oral fluid samples of a group of patients known to have periodontitis; (ii) subjecting the results obtained for said patients to a clustering technique so as to obtain two clusters, viz. a first defined cluster and a second non-defined cluster, so as to determine whether the measurement results for the subject fit with the first or the second cluster;

in the event of a subject fitting with the first cluster, subjecting a sample of oral fluid of said subject to a further measuring of protein concentrations, said proteins comprising IL1-β, IL6, and Collagen Telopeptide, thereby obtaining a testing value reflecting the joint concentrations measured for said proteins;

in the event of a subject fitting with the second cluster, optionally subjecting a sample of oral fluid of said subject to further measuring of the concentration of TIMP1, thereby obtaining a testing value reflecting the joint concentrations measured for said TIMP1 and the earlier measured concentration of HGF;

comparing the testing value obtained with a threshold value reflecting in the same manner the joint concentrations associated with advanced periodontitis, so as to assess whether the results are indicative for mild periodontitis or for advanced periodontitis in said subject.

In another aspect, the invention provides a method of detecting the proteins HGF, MMP8, and MMP9, and separately detecting (i) the proteins IL1-β, IL6, and Collagen Telopeptide or (ii) the protein TIMP1, comprising:

(a) obtaining an oral fluid sample from a human patient; and (b) detecting whether the proteins are present in the sample by contacting the sample with detection reagents for binding said proteins and detecting binding between each protein and the detection reagents.

In yet a further aspect, the invention provides the use of the proteins HGF, MMP8, and MMP9, and (i) the proteins IL1-β, IL6, and Collagen Telopeptide or (ii) the protein TIMP1 in an oral fluid sample or samples of a human patient, as biomarkers for assessing whether the patient has mild periodontitis or advanced periodontitis.

DETAILED DESCRIPTION OF THE INVENTION

In a general sense, the invention is based on the judicious insight to apply a clustering technique to a reference set of patient data, and then further discriminating the sets of biomarkers to be applied. This particularly aids in coping with the inherent non-homogeneity of patient populations.

The reference set can be obtained by collecting samples of oral fluid, such as saliva, of patients known to have periodontitis. This knowledge can be based on different diagnostics, particularly done in a conventional manner as done in examination by a dentist or other dental care professional. For the reference set, the concentrations of HGF, MMP8, MMP9 are measured. The results are then subjected to a clustering technique. This can refer to any such technique known to the skilled person. Thus, as an example, the "k-Means" clustering technique can applied to the concentration readings for HGF, MMP8 and MMP9. This results in cluster centres being obtained for each of the 2 clusters identified. E.g., for three biomarkers B1, B2, and B3:

$$\text{Cluster centre } C1 = \begin{bmatrix} B1_{C1} \\ B2_{C1} \\ B3_{C1} \end{bmatrix} \text{ and Cluster centre } C2 = \begin{bmatrix} B1_{C2} \\ B2_{C2} \\ B3_{C2} \end{bmatrix}$$

These cluster centres are computed from the biomarker readings of a number of T subjects where U subjects belong to Cluster C1 and T-U subjects belong to Cluster C2. The number T will be at least 2, such as generally at least 10, such as at least 20, such as at least 30, preferably at least 40. It is also conceivable to first select two or more data points from a larger set of clinical data, and then apply these selected data points to describe a cluster. The invention is particularly based on applying such clustering as to obtain two clusters. In such event, a first cluster is obtained which is a defined cluster. This refers to such a cluster as allows as many subjects as possible (i.e., the aforementioned number of U subjects) to show such similar results as to be expressed by a silhouette value of more than 0.8, such as more than 0.9, such as 0.95 or still closer to 1. By the same token, the corresponding cluster (for the T-U subjects) is non-defined, as expressed by silhouette values varying between 0 and 1.

In providing the invention, the inventors have further identified classifier models for both clusters, with reference to the results of a clinical study described below. Thereby it will be understood that, generally, any standard machine learning classifier can be used. In this disclosure, the classifying process is illustrated using the k-Nearest Neighbours classifier.

For cluster C1 using biomarkers IL1-β, IL6, Collagen Telopeptide as features for classification and k=7, results in an accuracy of 88.1% when classifying "mild periodontitis" and "advanced periodontitis".

For cluster C2 using biomarkers TIMP1 and HGF as features for classification and k=3, results in an accuracy of 81.25% when classifying "mild periodontitis" and "advanced periodontitis".

In carrying out the process of the invention, a sample of oral fluid of a subject to be tested is first subjected to a determination of the biomarkers associated with the clustering. Oral fluid generally refers to saliva or gingival crevicular fluid. A saliva sample can be saliva obtained from within the mouth, or obtained as spit. A saliva sample can also be a sample comprising saliva, as obtained by oral rinsing with a sampling rinse fluid, typically, e.g., sterile water, and then collecting the rinse, which then comprises saliva diluted with the rinse fluid. Hereinbefore and hereinafter, the term "oral fluid" may include saliva as such, spit, oral rinse comprising saliva, gingival crevicular fluid, and fluids comprising gingival crevicular fluid. Preferably, the oral fluid is a saliva sample. The term "saliva sample" includes saliva obtained from within the mouth, saliva obtained as spit, and saliva obtained from an oral rinse with a sampling fluid, such as sterile water. Hereinafter, general reference is just made to "a sample."

Next, a sample is subjected to a determination of the biomarkers selected for the actual classification of either of the two clusters. Thereby the two-stage test can be conducted using two samples, or two different drops of the same sample. Alternatively, a single sample is subjected to a determination of all of the biomarkers involved. The data for HGF, MMP8, and MMP9 are the subjected to data processing as desired, and subjected to comparison with the cluster centres as made available to the processing unit in the system used to carry out the invention. This comparison returns an indication to which cluster the subject belongs. If this is the first cluster, the data obtained for IL1-β, IL6, Collagen Telopeptide are processed and compared with a threshold value so as to determine the presence of mild or advanced periodontitis. If the subject belongs to the second cluster, the data obtained for HGF (which, in the event of a single sample is based on the same measurement as that applied in the aforementioned first stage of the process) and TIMP1 are processed and compared with a corresponding threshold value.

Alternatively, if the subject belongs to the second cluster, the test result is determined as being inconclusive. In such an embodiment, the invention (in all of its aspects) allows determining whether or not a subject is eligible for further testing in order to classify periodontitis in said subject. Subjects not belonging to the well-defined first cluster, will not, at that time, be sujected to further concentration measurement. This has the advantage of limiting the use of resources for further biomarker detection, as well as necessary further treatment, to only those subjects for whom the classification is likely to be the more accurate. Other subjects will then, in accordance with regular dental care practice, be monitored at a later stage.

The proteins applied in the invention are Hepatocyte Growth Factor (HGF), Matrix metalloproteinase 8 (MMP8), Matrix metalloproteinase 9 (MMP9), Interleukin-1β (IL1 (3), Interleukin-6 (IL6), Collagen Telopeptide, and metallopeptidase inhibitor 1 (TIMP1).

HGF is a paracrine cellular growth, motility and morphogenic factor. It is secreted by mesenchymal cells and targets and acts primarily upon epithelial cells and endothelial cells, but also acts on haemopoietic progenitor cells. HGF has been shown to have a major role in myogenesis and in wound healing. Its ability to stimulate mitogenesis, cell motility, and matrix invasion gives it a central role in angiogenesis, tumorogenesis, and tissue regeneration. HGF stimulates growth of epithelial cells and prevents regeneration of the connective tissue attachment. HGF is known as a serum marker indicating disease activity in various diseases.

IL-1β is a member of the interleukin 1 family of cytokines. This cytokine is produced by activated macrophages as a proprotein, which is proteolytically processed to its active form by caspase 1 (CASP VICE). This cytokine is an important mediator of the inflammatory response, and is involved in a variety of cellular activities, including cell proliferation, differentiation, and apoptosis.

IL-6 is an interleukin that acts as both a pro-inflammatory cytokine and an anti-inflammatory myokine. In humans, it is encoded by the IL6 gene. Interleukin 6 is secreted by T cells and macrophages to stimulate immune response, e.g. during infection and after trauma, especially burns or other tissue damage leading to inflammation. IL-6 also plays a role in fighting infection, as IL-6 has been shown in mice to be required for resistance against bacterium *Streptococcus pneumoniae*. In addition, osteoblasts secrete IL-6 to stimulate osteoclast formation. Smooth muscle cells in the tunica media of many blood vessels also produce IL-6 as a pro-inflammatory cytokine.

MMPs are a family of enzymes that are responsible for the degradation of extracellular matrix components such as collagen, proteoglycans, laminin, elastin, and fibronectin. They play a central role in the periodontal ligament (PDL) remodelling, both in physiological and pathological conditions. MMP-8, also known as neutrophil collagenase or PMNL collagenase (MNL-CL), is a collagen protease enzyme which is present in the connective tissue of most mammals.

MMP-9, also known as 92 kDa type IV collagenase, 92 kDa gelatinase or gelatinase B (GELB), is a matrixin, a class of enzymes that belong to the zinc-metalloproteinases family involved in the degradation of the extracellular matrix. TIMP1 is an inhibitory molecule that regulates matrix metalloproteinases (MMPs), and disintegrin-metalloproteinases (ADAMs and ADAMTSs). In regulating MMPs, TIMP1 plays a crucial role in extracellular matrix (ECM) composition, wound healing, and pregnancy.

The seven proteins mentioned above are known in the art. The skilled person is aware of their structure, and of methods to detect them in an aqueous sample, such as an oral fluid sample. Hereinafter the aforementioned protein biomarkers are collectively referred to as "the biomarker panels of the invention." A biomarker panel of the invention, in one embodiment, consist of the three sets of protein biomarkers discussed above.

Preferably, a biomarker panel of the invention consists of not more than the protein biomarkers identified in each set of the invention. In addition to the biomarker panels of the invention, other biomarkers and or data, such as demographic data (e.g., age, sex) can be included in a set of data applied for the determination of the type of periodontitis.

However, a desirable advantage of the present invention is that the classification of periodontitis in a subject can be determined by measuring preferably not more than the seven biomarkers identified above. Or, if not all of the biomarkers are measured in the same sample, only six different biomarkers in the event of the first cluster (HGF, MMP8, MMP9, IL1-β, IL6, and Collagen Telopeptide), or only four different biomarkers in the event of the second cluster (HGF, MMP8, MMP9 and TIMP1). Particularly, the determination does not need to involve the use of other data, which advantageously provides a simple and straightforward diagnostic test.

The method, as desired, requires only that a small sample, e.g. a dropsize, is taken from the subject. As discussed above, this can refer to a single sample or to two different samples for either stage. The size of the sample will typically range of from 0.1 μl to 2 ml, such as 1-2 ml, whereby smaller amounts, e.g., 0.1 to 100 μl can be used for in vitro device processing, and whereby taking a larger sample, such as up to 20 ml, such as 7.5 to 17 ml, is also possible.

This sample is entered into an in vitro diagnostic device, which measures the concentrations of the proteins involved, and which, in two stages as discussed, returns a diagnostic outcome, classifying the subject on the basis of a likelihood of having mild periodontitis or advanced periodontitis.

The ease of use of this invention will make it possible to test the majority of dental patients with periodontitis, or with a high risk for developing periodontitis, on a regular basis (e.g. as part of a regular dental check or even at home). This allows, inter alia, detecting the presence of mild periodontitis before it proceeds to advanced periodontitis, and thus enables more timely taking oral care measures to prevent periodontitis from advancing. Or, e.g., with patients known to be at high risk for periodontitis, and tested for the first time, the method allows to identify whether the periodontitis is mild or advanced. Also, the method can be applied after treatment of a patient previously diagnosed with advanced periodontitis, in order to check whether the periodontitis has improved so as to become mild. Particularly, the method is also suitable for self-diagnosis, whereby the steps of taking the sample and entering it into a device can be conducted by the patient him- or herself.

The patient may typically be suspected or known to have periodontitis when the invention is carried out to determine whether the periodontitis is mild or advanced. In certain embodiments therefore, the method is for assessing whether a human patient, suspected or known to have periodontitis, has mild periodontitis or advanced periodontitis.

A method of the invention typically comprises detecting the aforementioned proteins making up the applicable biomarker panels, and optional further biomarker proteins, by using one or more detection reagents.

By "detecting" is meant measuring, quantifying, scoring, or assaying the concentration of the biomarker proteins. Methods of evaluating biological compounds, including biomarker proteins, are known in the art. It is recognized that methods of detecting a protein biomarker include direct measurements and indirect measurements. One skilled in the art will be able to select an appropriate method of assaying a particular biomarker protein.

The term "concentration" with respect to the protein biomarkers is to be given its usual meaning, namely the abundance of the protein in a volume. Protein concentration is typically measured in mass per volume, most typically mg/ml or μg/ml, but sometimes as low as pg/ml. An alternative measure is Molarity (or Molar concentration), mon or "M". The concentration can be determined by detecting the amount of protein in a sample of known, determined or pre-determined volume.

An alternative to determining the concentration is to determine the absolute amount of the protein biomarker in the sample, or determining the mass-fraction of the biomarker in the sample, for example the amount of the biomarker relative to the total of all other proteins in the sample.

A "detection reagent" is an agent or compound that specifically (or selectively) binds to, interacts with or detects the protein biomarker of interest. Such detection reagents may include, but are not limited to, an antibody, polyclonal antibody, or monoclonal antibody that preferentially binds the protein biomarker.

The phrase "specifically (or selectively) binds" or "specifically (or selectively) immunoreactive with," when referring to a detection reagent, refers to a binding reaction that is determinative of the presence of the protein biomarker in a heterogeneous population of proteins and other biologics. Thus, under designated immunoassay conditions, the specified detection reagent (e.g. antibody) binds to a particular protein at least two times the background and does not substantially bind in a significant amount to other proteins present in the sample. Specific binding under such conditions may require an antibody that is selected for its specificity for a particular protein. A variety of immunoassay formats may be used to select antibodies specifically immunoreactive with a particular protein. For example, solid-phase ELISA immunoassays (enzyme linked immunosorbent assay) are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice the background signal or noise and more typically more than 10 to 100 times the background.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region. The antibody may be a bispecific antibody, e.g. an antibody that has a first variable region that specifically binds to a first antigen and a second variable region that specifically binds to a second, different, antigen. Use of at least one bispecific antibody can reduce the number of detection reagents needed.

Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive.

The biomarker proteins of the invention can be detected in a sample by any means. Preferred methods for biomarker detection are antibody-based assays, protein array assays, mass spectrometry (MS) based assays, and (near) infrared spectroscopy based assays. For example, immunoassays, include but are not limited to competitive and non-competitive assay systems using techniques such as Western blots, radioimmunoassays, ELISA, "sandwich" immunoassays, immunoprecipitation assays, precipitin reactions, gel diffusion precipitin reactions, immunodiffusion assays, fluorescent immunoassays and the like. Such assays are routine and well known in the art. Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding an antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and re-suspending the beads in SDS/sample buffer. The ability of the antibody to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with Sepharose beads).

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise.

ELISAs typically comprise preparing antigen (i.e. the biomarker protein of interest or fragment thereof), coating the well of a 96-well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art.

Since multiple markers are used, in the second stage of the process of the invention, a threshold is determined on the basis of the joint concentrations of these biomarkers. This threshold determines whether a subject is classified as having mild periodontitis or advanced periodontitis. The invention reflects the insight that periodontitis can be detected, as being mild or advanced, with sufficient accuracy based on a measurement of the combination of biomarkers as indicated above.

The second stage of the method of the invention comprises determining a testing value reflecting the joint concentrations measured for said proteins. A joint concentration value can be any value obtained by input of the concentrations as determined and an arithmetic operation of these values. This can, e.g., be a simple addition of the concentrations. It can also involve multiplying each concentration with a factor reflecting a desired weight of these concentrations, and then adding up the results. It can also involve multiplying the concentrations with each other, or any combination of multiplication, division, subtraction, exponentiation, and addition. It can further involve raising concentrations to some power.

The resulting joint concentration value is compared with a threshold value reflecting in the same manner the joint concentrations associated with the presence of advanced periodontitis. The comparison allows assessing whether the testing value is indicative of the presence of advanced periodontitis in the subjects whose saliva is subjected to the test, or of mild periodontitis.

The threshold value can, e.g., be the joint concentration value, obtained in the same manner on the basis of the concentrations determined for the same proteins in a reference sample associated with the presence of advanced periodontitis, i.e. in a subject diagnosed with advanced periodontitis. Typically, thereby a value reflecting the same or higher joint concentration is indicative of the presence of advanced periodontitis in a tested subject. Analogously, a value reflecting a lower joint concentration in the saliva of a tested periodontitis subject, indicates that the periodontitis is mild or moderate (i.e., not advanced). However, it will be understood that it is also possible to calculate a threshold value (e.g. by using a negative multiplier) such that a testing value indicating advanced periodontitis would be below the threshold, and a testing value indicating mild periodontitis, would be above the threshold.

The threshold value can also be determined on the basis of measuring the concentrations of the present biomarker proteins in a set of samples, including patients with a known diagnosis of advanced periodontitis and not advanced (mild and/or moderate) periodontitis. Thereby the measured concentration values can be subjected to statistical analysis, possibly including machine learning methods, allowing to discriminate, with the desired sensitivity and specificity, subjects classified as having mild or moderate periodontitis and subjects classified as patients suffering from advanced periodontitis. Therefrom, the desired threshold value can be obtained. On the basis of this threshold value, a sample to be tested can be subjected to the same concentration measurement, and the concentration values are then processed, in the same manner in which the threshold value is obtained, so as to determine a joint concentration value that can be compared with the threshold, thus allowing the tested sample to be classified as having mild or advanced periodontitis.

In an interesting embodiment, the joint concentration value is obtained in the form of a score as follows. A numerical value (protein concentration values in e.g. ng/ml) is assigned to each measurement, and these values are used in a linear or non-linear combination to calculate a score between zero and one. In the event that the threshold value is determined on the basis of a set of subjects as mentioned above, the score between 0 and 1 is typically calculated with the sigmoid function that takes the joint concentration as input (as shown further on).

When the score exceeds a certain threshold, the method indicates that the subject has advanced periodontitis. The threshold may be chosen based on the desired sensitivity and specificity.

It will be understood that in performing a 'mild or advanced periodontitis classification' on a subject, in accordance with the invention, this is on subjects that are suspected to have periodontitis. This can either be based on, e.g., a previously performed diagnosis of periodontitis, though perhaps without ability to differentiate the extent of it, or, e.g., suspected from the subject's oral health condition record. Nonetheless, the first stage of the biomarker measurements, i.e., measuring the concentrations of HGF, MMP8, and MMP9, can also be used to assess both whether a subject has in fact periodontitis, and whether or not said subject is a patient belonging to the first cluster.

Clinical definitions as acknowledged in the art are based on the following:

Gingival Index (GI)

A full mouth gingival index will be recorded based on the Lobene Modified Gingival Index (MGI) rated on a scale of 0 to 4, where:
0=absence of inflammation,
1=mild inflammation; slight change in colour little change in texture of any portion of but not the entire margin or papillary gingival unit,
2=mild inflammation; but involving entire margin or papillary unit,
3=moderate inflammation; glazing, redness, oedema and/or hypertrophy of margin or papillary unit,
4=severe inflammation; marked redness, oedema and/or hypertrophy of marginal or papillary gingival unit, spontaneous bleeding, congestion, or ulceration].

Probing Depths (PD)

Probing depths will be recorded to the nearest mm using a manual UNC-15 periodontal probe. Probing depth is the distance from the probe tip (assumed to be at the base of the pocket) to the free gingival margin.

Gingival Recession (REC)

Gingival recession will be recorded to the nearest mm using a manual UNC-15 periodontal probe. Gingival recession is the distance from the free gingival margin to the cemento-enamel junction. Gingival recession will be indicated as a positive number and gingival overgrowth will be indicated as a negative number.

Clinical Attachment Loss (CAL)

Clinical attachment loss will be calculated as the sum of probing depth+recession at each site Bleeding on Probing (BOP)

Following probing, each site will be assessed for bleeding on probing, if bleeding occurs within 30s of probing, a score of 1 will be assigned for the site, otherwise, a score of 0 will be assigned.

The resulting subject group (patient group) definition is as follows, whereby the mild-moderate periodontitis group and the advanced periodontitis group are relevant to the present invention:

Healthy group (H): PD≤3 mm in all sites (but would allow up to four 4 mm pockets at distal of last standing molars), no sites with interproximal attachment loss, GI of ≥2.0 in ≤10% sites, % BOP scores≤10%;

Gingivitis group (G): GI≥3.0 in >30% of sites, no sites with interproximal attachment loss, no sites with PD>4 mm, % BOP scores>10%;

Mild-moderate periodontitis group (MP): interproximal PD of 5-7 mm, (equating to approximately 2-4 mm CAL) at ≥8 teeth, % BOP scores>30%

Advanced periodontitis group (AP): interproximal PD of ≥7 mm, (equating to approximately ≥5 mm CAL) at ≥12 teeth, % BOP scores>30%

Figure 1:
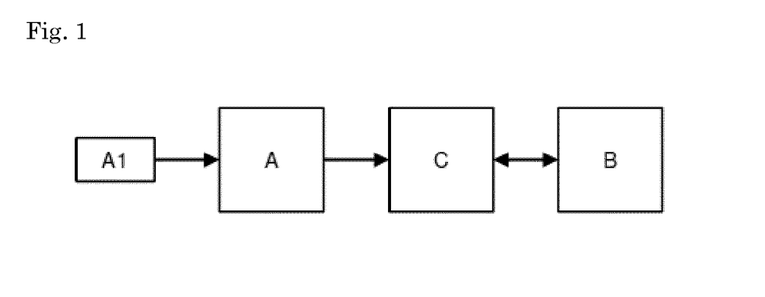
FIG. 1 schematically represents a system for use in the method as described in this disclosure.

In an embodiment, the method of the invention makes use of a system as represented schematically in FIG. 1. The system can be a single apparatus having various device components (units) integrated therein. The system can also have its various components, or some of these components, as separate apparatuses. The components shown in FIG. 1 are a measurement device (A), a graphical user interface (B) and a computer processing unit (C).

As mentioned above, the system of the invention comprises a data connection to an interface, whereby the interface itself can be a part of the system or can be a remote interface. The latter refers to the possibility to use a different apparatus, preferably a handheld apparatus such as a smartphone or a tablet computer, for providing the actual interface. The data connection in such cases will preferably involve wireless data transfer such as by Wi-Fi or Bluetooth, or by other techniques or standards.

The measurement device (A) is configured to receive a sample, or more samples, for example by putting a drop of saliva on a cartridge (A1), which can be inserted into the device (A). The device can be an existing device that is capable to determine, from the same sample, the concentrations of the applicable proteins. As discussed above, this can refer to a measurement of all of the seven proteins possibly involved in the two stages of the method carried out in the system of the invention. It can also refer to different units, each configured to determine any of the three different sets of protein biomarkers involved (i.e.: [HGF, MMP8, MMP9], [IL1-β, IL6, Collagen Telopeptide], and [HGF, TIMP1]).

The processing unit (C) receives numerical values for the protein concentrations from part (A). The unit (C) is provided with software (typically embedded software) allowing it to carry out the two stages of the method of the invention. For the first stage this results in a comparison with cluster centres.

If, e.g., a new patient's biomarker readings are as follows:

$$\text{Patient } P1 = \begin{bmatrix} B1_{P1} \\ B2_{P1} \\ \vdots \\ BN_{P1} \end{bmatrix}$$

The distance between Patient P1's readings and Clusters C1 and C2 is computed. There are various distance metrics but in this disclosure an example is using the Euclidean distance.

Distance between P1 and C1:

$$d(P1, C1) = \sqrt{(B1_{P1} - B1_{C1})^2 + (B2_{P1} - B2_{C1})^2 + \cdots + (BN_{P1} - BN_{C1})^2}$$

Distance between P1 and C2:

$$d(P2, C2) = \sqrt{(B1_{P1} - B1_{C2})^2 + (B2_{P1} - B2_{C2})^2 + \cdots + (BN_{P1} - BN_{C2})^2}$$

If $d(P1,C1) \leq d(P2,C2)$, P1 belongs to C1. Similarly, if $d(P1,C1) > d(P2,C2)$, P1 belongs to C2.

Figure 4:
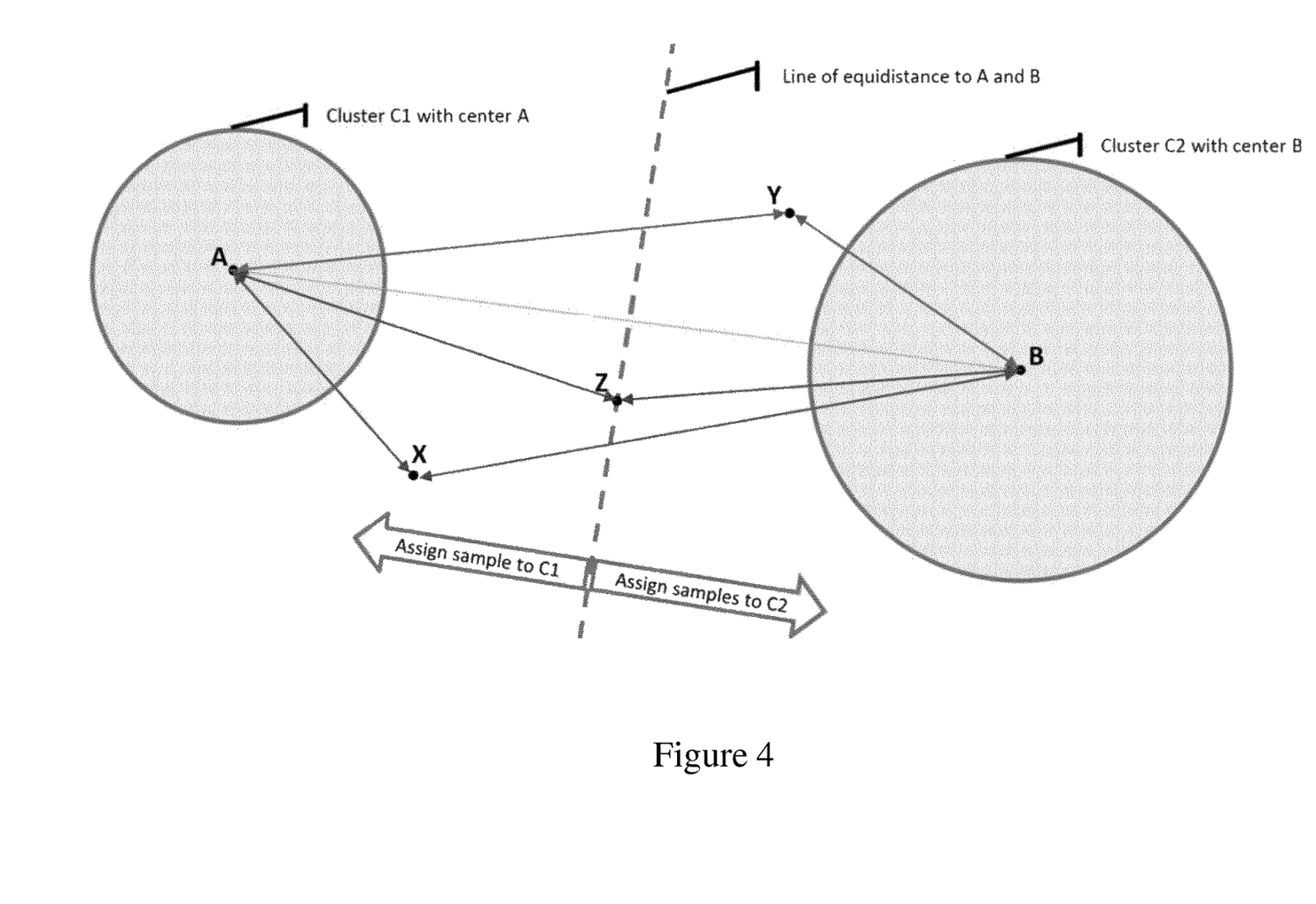
FIG. 4 illustrates how to assign a sample score to Cluster 1 or Cluster 2.

This comparison with cluster centres can be depicted as in FIG. 4. Here, individual sample Q (here: X,Y,Z as illustration) needs assignment to a cluster. There are 3 options:
1. Cluster C1 if distance A-Q<distance B-Q: point X
2. Cluster C2 if distance A-Q>distance B-Q: point Y
3. Undefined if distance A-Q=distance B-Q: point Z (note: here, assigned to C1).

For the second stage, unit C is configured to calculate a score (S) between 0 and 1. The software further includes a numerical value for the threshold (T). If the calculated value (S) exceeds (T), unit (C) will output an indication (I) of 'advanced periodontitis' to the GUI (B), otherwise it will output 'mild periodontitis'. A further embodiment may use the specific value of (S) to indicate the certainty with which the indication (I) is made. This can be a probability score, whereby 0.5 is a possible threshold value, and e.g. a score S=0.8 would indicate the probability of advanced periodontitis. Interesting options are:

Based on the score S, one can directly indicate a certainty, i.e. S=0.8 means 80% certainty of advanced periodontitis;

Based on the score S one can make a binary or tertiary indication:
S<T→mild periodontitis, S≥T→advanced periodontitis;
S<R1→mild periodontitis, R1≤S<R2→inconclusive, S≥R2→advanced periodontitis;

In addition, it is possible to attach a certainty to such a binary or tertiary indication. This certainty will be determined by the distance of the score S from the chosen threshold(s) (T,R1,R2).

A specific calculation of the score can be implemented, e.g., by means of a sigmoid function applying the following formula:

$$S = \frac{1}{1 + \exp\left(-\left(c_0 + \sum_{i=1}^{N} c_i B_i\right)\right)}$$

Therein N is the number of proteins/biomarkers used. $c_0$, $c_1$, etc. are coefficients (numerical values) and $B_1$, $B_2$, etc. are the respective protein concentrations.

Determining of the coefficients can be done by a training procedure:

Select N1 subjects with advanced periodontitis and N2 subjects with mild periodontitis.

The subjects without mild periodontitis are considered to have score S=0, the subjects with advanced periodontitis are considered to have score S=1.

Take a sample from each subject and determine the protein concentrations of a combination of biomarkers as explained above Perform logistic regression between the protein concentrations and the scores.

Other regression or machine learning methods (linear regression, neural network, support vector machine, logistic regression) may be used to train a classifier that predicts whether a subject has gingivitis or a healthy oral condition based on the protein concentrations.

With reference to the aforementioned system, the invention also provides, in a further aspect, a system for classifying a human subject as having mild periodontitis or advanced periodontitis. The system comprises
detection means configured to measure in an oral fluid sample of the subject the concentrations of the biomarkers Hepatocyte Growth Factor (HGF), Matrix metalloproteinase 8 (MMP8), Matrix metalloproteinase 9 (MMP9), Interleukin-1β (IL1β), Interleukin-6 (IL6), Collagen Telopeptide, and metallopeptidase inhibitor 1 (TIMP1);
one or more processing units configured to determine a classification result from the measured concentrations of biomarkers in an oral fluid sample of the subject;

Optionally, a data connection allowing results obtained from the one or more processing units to be directed to an interface, particularly a graphical user interface, capable of presenting information, said interface being either a part of the system or a remote interface;

As explained above, protein detection means are known, and easily accessible to the skilled person. Typically, there is provided one or more containers for receiving the oral sample of a subject therein, the container provided with the detection means. The optional interface (or a data connection to remote interface), particularly is a graphical user interface (GUI), capable of presenting information; a GUI is a type of user interface that allows users to interact with electronic devices through graphical icons and visual indicators such as secondary notation, instead of text-based user interfaces, typed command labels or text navigation (none of such interface types being excluded in the present invention); GUIs are generally known, and are used typically in handheld mobile devices such as MP3 players, portable media players, gaming devices, smartphones and smaller household, office and industrial controls; as said, the interface optionally can also be chosen so as to be capable of putting in information, such as, e.g., the age of the subject, sex, BMI (Body Mass Index);

The processor is able and adapted to determine from the detected concentration of the set of biomarkers in an oral sample of the subject a diagnosis result comprising an indication of the cluster to which the subject belongs, as well as in the second stage, whether the subject is classified as having mild periodontitis or advanced periodontitis.

The invention also provides, either separately or as part of the aforementioned system, a kit for determining the concentration of biomarkers for periodontitis in saliva, The kit comprises seven detection reagents, each detection reagent directed to a different biomarker, wherein the detection reagents are capable of binding, respectively, HGF, MMP8, MMP9, IL1-β, IL6, Collagen Telopeptide, and TIMP1, and wherein the kit is configured to as to separately process the concentrations of three different sets of said biomarkers, viz. a first set comprising HGF, MMP8, and MMP9, a second set comprising IL1-β, IL6, and Collagen Telopeptide, and a third set comprising TIMP1 and HGF. As discussed above with reference to the method of the invention, the kit may either comprise separate sets of detection reagents for the three separate sets of biomarkers, or one set of detection reagents for all of the biomarkers involved. In the latter case, a processing unit is configured so as to process the results of the concentration measurements so as to reflect the relevant sets of biomarkers.

Preferably said kits comprise a solid support, such as a chip, a microtiter plate or a bead or resin comprising said detection reagents. In some embodiments, the kits comprise mass spectrometry probes, such as ProteinChip™.

The kits may also provide washing solutions and/or detection reagents specific for either unbound detection reagent or for said biomarkers (sandwich type assay).

The invention also provides a method of diagnosing whether a human patient suspected of having periodontitis has mild periodontitis or advanced periodontitis, on the basis of the concentrations of proteins in a sample of oral fluid from the patient, the method comprising:

measuring in a sample of oral fluid of the human patient the concentrations of the proteins HGF, MMP8, and MMP9;

comparing the measurement results with cluster centres obtained by (i) determining the concentrations of the proteins HGF, MMP8, and MMP9 in oral fluid samples of a group of patients known to have periodontitis; (ii) subjecting the results obtained for said patients to a clustering technique so as to obtain two clusters, viz. a first defined cluster and a second non-defined cluster, so as to determine whether the measurement results for the subject fit with the first or the second cluster;

in the event of a subject fitting with the first cluster, subjecting a sample of oral fluid of said subject to a further measuring of protein concentrations, said proteins comprising IL1-β, IL6, and Collagen Telopeptide, thereby obtaining a testing value reflecting the joint concentrations measured for said proteins;

in the event of a subject fitting with the second cluster, optionally subjecting a sample of oral fluid of said subject to further measuring of the concentration of TIMP1, thereby obtaining a testing value reflecting the joint concentrations measured for said TIMP1 and the earlier measured concentration of HGF;

comparing the testing value obtained with a threshold value reflecting in the same manner the joint concentrations associated with advanced periodontitis, so as to assess whether the results are indicative for mild periodontitis or for advanced periodontitis in said subject.

Optionally, the method of this aspect comprises the further step of treating the periodontitis in the patient. This optional treatment step can comprise the administration of known therapeutic agents or dental procedures, or a combination of therapeutic agents and dental procedures. Known therapeutic agents include the administration of antimicrobial-containing agents such as a mouthwash, chip, gel or microsphere. A typical antimicrobial agent for use in treating periodontitis is chlorhexidine. Other therapeutic agents include antibiotics, typically orally-administered antibiotics, and enzyme suppressants such as doxycycline. Known non-surgical therapeutic procedures include scaling and root planing (SRP). Known surgical procedures include surgical pocket reduction, flap surgery, gum grafts or bone grafts.

The invention further provides a method of detecting the proteins HGF, MMP8, and MMP9, and separately detecting (i) the proteins IL1-0, IL6, and Collagen Telopeptide or (ii) the protein TIMP1, comprising:

(a) obtaining an oral fluid sample from a human patient; and (b) detecting whether the proteins are present in the sample by contacting the sample with detection reagents for binding said proteins and detecting binding between each protein and the detection reagents.

The invention will be further illustrated with reference to the following non-limiting example.

Example

In a clinical study with 58 subjects, there were 31 patients diagnosed with mild periodontitis and 27 from advanced periodontitis. K-means clustering was used to cluster all subjects using HGF, MMP8 and MMP9. Note that k was varied from 2 to 10. For every k, the average silhouette value was computed over all 58 subjects.

The silhouette coefficient combines both cohesion and separation (ref. cs.fit.edu/~pkc/classes/ml-internet/silhouette.pdf). The following steps explain how to compute the silhouette coefficient for an individual point, a process that consists of the following three steps.

1. For the $i^{th}$ object, calculate its average distance to all other objects in its cluster. Call this value $a_i$.
2. For the $i^{th}$ object and any cluster not containing the object, calculate the object's average distance to all the objects in the given cluster. Find the minimum such value with respect to all clusters; call this value bi.
3. For the $i^{th}$ object, the silhouette coefficient is $s_i=(b_i-a_i)/\max(a_i,b_i)$.

The value of the silhouette coefficient can vary between −1 and 1. A negative value is undesirable because this corresponds to a case in which $a_i$, the average distance to points in the cluster, is greater than $b_i$, the minimum average distance to points in another cluster. We want the silhouette coefficient to be positive ($a_i<b_i$), and for $a_i$ to be as close to 0 as possible, since the coefficient assumes its maximum value of 1 when $a_i=0$.

The average silhouette coefficient of a cluster can be computed by simply taking the average of the silhouette coefficients of points belonging to the cluster. An overall measure of the goodness of a clustering can be obtained by computing the average silhouette coefficient of all points.

Figure 2:
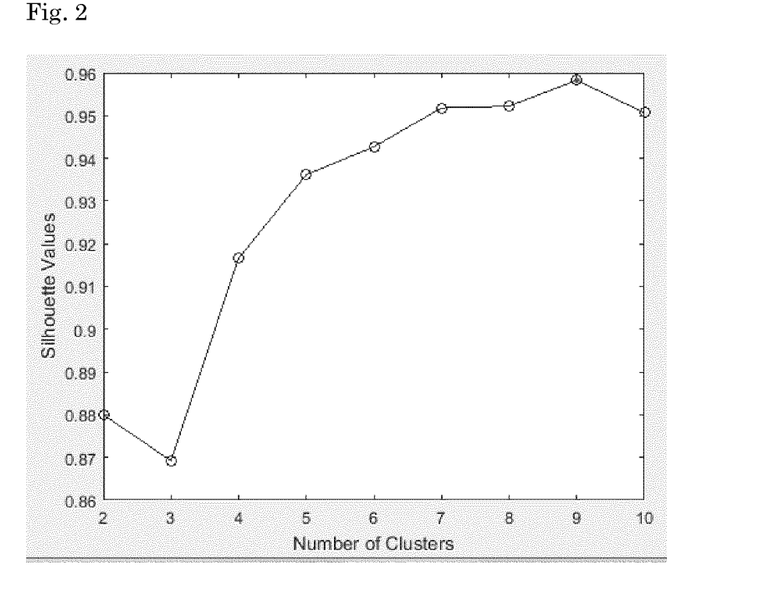
FIG. 2 is a graph illustrating silhouette values.
Figure 3:
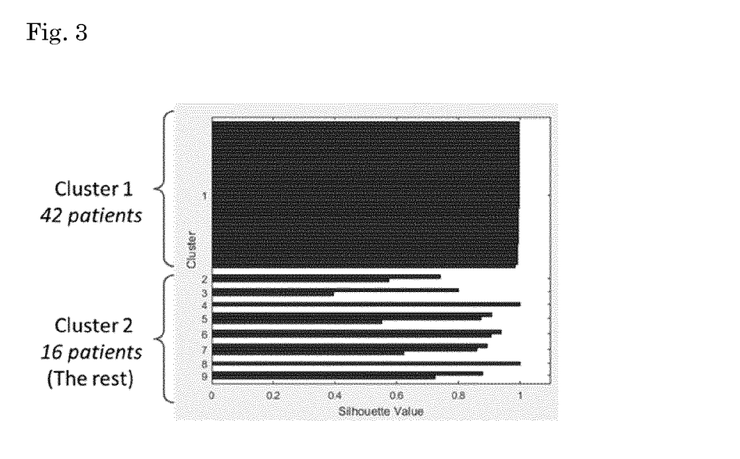
FIG. 3 illustrates the result of the clustering of patient population data.

FIG. 2 illustrates average silhouette values as the value of k was varied from 2 to 10. The figure clearly shows that the maximum silhouette value was attained when k=9. The silhouette plot for k=9 is shown in FIG. 3.

The silhouette plot illustrates that Cluster 1 is very well defined as its average is very close to 1. In order to define Cluster 1, the following two conditions need to be met:

The chosen cluster should have the highest average silhouette value

The chosen cluster should contain at least 40% of all the data points (In this specific example, 42 out of 58 patients (i.e. 72%) fall within Cluster 1)

The other points, however, do not form any clear and distinct clusters. Thus, the points which do not fall in Cluster 1 are all placed in Cluster 2. Cluster 2 is referred to as the non-defined cluster.

Once the clusters have been defined, the next steps are to identify which cluster a patient belongs to and then to perform the classification in order to assess if the patient is suffering from mild or advanced periodontitis using the appropriate list of biomarkers. The details of these steps are described below:

Phase 1: Measure the concentrations of HGF, MMP8 and MMP9 (or any combinations of these). The obtained readings are used to decide if the patient belongs to a Cluster C1 or Cluster C2.

Phase 2: Measure the concentrations of certain proteins depending on whether the patient in Phase 1 belongs to Cluster C1 or Cluster C2

If the patient belongs to Cluster C1, the top three protein biomarkers which can be used to classify mild/advanced periodontitis are: IL1-0, IL6 and Collagen Telopeptide.

The table below shows the accuracy results for Cluster 1 (based on a clinical study with 42 patients) using different combinations of the top three protein biomarkers mentioned above:

$$\text{Note: Accuracy} = \frac{\Sigma \text{ True positive } (MP) + \Sigma \text{ True negative } (AP)}{\Sigma \text{Total population } (MP \text{ and } AP)} \text{ based on a confusion matrix}$$

| No. | Biomarker(s) | Accuracy (%) |
|---|---|---|
| | IL1-β | 64.29 |
| | IL6 | 66.67 |
| | Collagen Telopeptide | 66.67 |
| | IL1-β, IL6 | 66.67 |
| | IL1-β, Collagen Telopeptide | 66.67 |
| | IL6, Collagen Telopeptide | 78.57 |
| | IL1-β, IL6, Collagen Telopeptide | 88.10 |

Thus if a patient belongs to Cluster 1, IL1-β, IL6, Collagen Telopeptide are the biomarkers that would allow a patient to be identified with mild periodontitis or advanced periodontitis with an accuracy of 88.1%. Similarly, using only IL6 and Collagen Telopeptide results in an accuracy of 78.6%.

If the patient belongs to Cluster C2, the top three protein biomarkers which can be used to classify mild/advanced periodontitis are: TIMP1 and HGF.

The table below shows the accuracy results for Cluster 2 (based on a clinical study with 16 patients) using different combinations of the top three protein biomarkers mentioned above:

| No. | Biomarker(s) | Accuracy (%) |
|---|---|---|
| | IL6_d | 68.75 |
| | TIMP1 | 81.25 |
| | HGF | 56.25 |
| | IL6_d, TIMP1 | 62.5 |
| | IL6_d, HGF | 68.75 |
| | TIMP1, HGF | 81.25 |
| | IL6_d, TIMP1, HGF | 81.25 |

It is noted that IL6d refers to the difference of the IL6 readings taken prior to and after the treatment of a patient. As can be seen, the selection of TIMP1 and HGF as the biomarkers to be determined, obviates the need for taking into account the (more complicated) determination of a difference between two measurement values.

While the invention has been illustrated and described in detail in the drawings and foregoing description, such illustration and description are to be considered illustrative or exemplary and not restrictive; the invention is not limited to the disclosed embodiments.

For example, it is possible to present detection reagents for different biomarkers in different units. Or, conveniently, a kit of the invention can comprise a fixed set of detection reagents for the protein biomarkers that are used in the first stage, i.e., HGF, MMP-8, and MMP-9, and flexible (separate) modules comprising a detection reagent for either or both of the two sets used in the second stage. In a further alternative, a single separate module can be used for all four of the second stage biomarkers.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage. Any reference signs in the claims should not be construed as limiting the scope.

In sum, we hereby disclose a system and an in vitro method for assessing whether a human subject suffering from periodontitis has mild periodontitis or advanced periodontitis. The system and method are based on the insight to apply a clustering technique to a reference set of patient data, and then further discriminating the sets of biomarkers to be applied. The clusters are determined on the basis of the biomarkers Hepatocyte Growth Factor (HGF), Matrix metalloproteinase 8 (MMP8), and Matrix metalloproteinase 9 (MMP9). The actual classification of the subject is done on the basis of the measurement of the concentrations of either of two sets of biomarkers. For one cluster these are Interleukin-1β (IL1β), Interleukin-6 (IL6), and Collagen Telopeptide. For the other cluster, these are HGF and metallopeptidase inhibitor 1 (TIMP1).

The invention claimed is:

1. A system for classifying a human subject as having mild periodontitis or advanced periodontitis, the system comprising:
    at least one detector configured to measure concentrations of biomarkers in a sample of oral fluid of the subject, the biomarkers including Hepatocyte Growth Factor (HGF), Matrix metalloproteinase 8 (MMP8), Matrix metalloproteinase 9 (MMP9), Interleukin-1β (IL1β), Interleukin-6 (IL6), and Collagen Telopeptide; and
    one or more processors configured to interface with the at least one detector to receive the measured concentrations of the biomarkers in the sample of oral fluid of the subject;
    wherein, in a first stage, the at least one detector is configured to measure first-stage concentrations of a first set of biomarkers comprising HGF, MMP8, and MMP9 to obtain a first measurement result of the first-stage concentrations,
    wherein the one or more processors are configured to process the first-stage concentrations to determine whether to measure, in a second stage, second-stage concentrations of a second set of biomarkers comprising IL1-β, IL6, and Collagen Telopeptide,
    wherein the at least one detector is configured to obtain a second measurement result of the second-stage concentrations when the one or more processors determine to measure the second-stage concentrations, and
    wherein the one or more processors are configured to process the second-stage concentrations to determine a classification result including an indication of mild periodontitis or advanced periodontitis, the classification result enabling determination of a treatment of the subject.

2. The system according to claim 1, wherein the human subject is suspected to have periodontitis.

3. The system according to claim 1, further comprising:
    one or more containers for receiving the sample of oral fluid of the subject therein, said one or more containers being provided with the at least one detector configured to measure the concentrations of the biomarkers in the sample of oral fluid.

4. The system according to claim 1, further comprising:
    a user interface for presenting the indication of mild periodontitis or advanced periodontitis to a user; and
    a data connection between the one or more processors and the user interface for transferring the indication of mild periodontitis or advanced periodontitis from the processor to the user interface.

5. The system according to claim 1, further comprising:
    a single container configured to receive the sample of oral fluid, the single container being provided with the detector configured to measure the concentrations of the biomarkers in the sample of oral fluid.

6. The system according to claim 1, further comprising:
    a first container configured to receive a portion of the sample of oral fluid sample, the first container being provided with a first detector of the at least one detector configured to measure the concentrations of HGF, MMP8, and MMP9,
    a second container configured to receive another portion of the sample of oral fluid, the second container being provided with a second detector of the at least one detector configured to measure the concentrations of IL1-β, IL6, and Collagen Telopeptide, and a third container configured to measure the concentrations of HGF and TIMP-1.

7. The system according to claim 6, wherein the second container is a separate module insertable in to the system.

8. The system according to claim 1, wherein the one or more processors are enabled to function by means of an internet-based application.

9. A method for assessing whether a subject has mild periodontitis or advanced periodontitis, the method comprising:
    measuring in a sample of oral fluid from said subject concentrations of proteins HGF, MMP8, and MMP9 to obtain measurement results;
    comparing, using a processing unit, the measurement results with cluster centres to determine whether the measurement results for the subject fit with a first cluster or a second cluster, wherein the cluster centres are obtained by (i) determining concentrations of the proteins HGF, MMP8, and MMP9 in oral fluid samples of patients known to have periodontitis; and (ii) subjecting the determined concentrations for said patients to a clustering technique to obtain the first cluster and the second cluster, wherein the first cluster is a defined cluster and the second cluster is a non-defined cluster;
    when the measurement results fit with the first cluster, further measuring in a sample of oral fluid from said subject concentrations of additional proteins comprising IL1-β, IL6, and Collagen Telopeptide, thereby obtaining a first testing value reflecting joint concentrations measured for said additional proteins;
    when the measurement results fit with the second cluster, further measuring in a sample of oral fluid of said subject concentration of TIMP1, thereby obtaining a second testing value reflecting joint concentrations measured for said TIMP1 and the earlier measured concentration of the protein HGF;
    comparing, using a processor, the first testing value or the second testing value with a threshold value reflecting corresponding joint concentrations associated with advanced periodontitis, so as to assess whether the first testing value or the second testing value is indicative of mild periodontitis or advanced periodontitis in said subject; and
    determining of a treatment of the subject based on the indication of mild periodontitis or advanced periodontitis.

10. The method according to claim 9, wherein the subject is suspected to have periodontitis.

11. The method according to claim 9, wherein the threshold value is based on concentrations determined for HGF, MMP8, MMP9, IL1-β, IL6, and Collagen Telopeptide in a reference sample associated with presence of advanced periodontitis.

12. A kit for determining concentrations of biomarkers for periodontitis in saliva, said kit comprising:
    seven detection reagents, each detection reagent directed to a different biomarker, wherein the detection reagents are capable of binding, respectively, HGF, MMP8, MMP9, IL1-β, IL6, Collagen Telopeptide, and TIMP1, and wherein the kit is configured to as to separately process concentrations of three different sets of said biomarkers, wherein a first set comprises HGF, MMP8, and MMP9, a second set comprises IL1-β, IL6, and Collagen Telopeptide, and a third set comprises TIMP1 and HGF, and wherein said detection reagents are contained on a chip, a microtiter plate, a bead or a resin.

13. A method of diagnosing whether a human patient suspected of having periodontitis has mild periodontitis or advanced periodontitis based on concentrations of proteins in a sample of oral fluid from the human patient, the method comprising:

measuring in the sample of oral fluid from the human patient concentrations of proteins HGF, MMP8, and MMP9 to obtain measurement results;

comparing, using a processing unit, the measurement results with cluster centres obtained by (i) determining concentrations of proteins HGF, MMP8, and MMP9 in oral fluid samples of patients known to have periodontitis; (ii) subjecting the determined concentrations to a clustering technique to obtain a defined cluster and a non-defined cluster;

determining whether the measurement results for the human patient fit with the defined cluster or the non-defined cluster;

when the human patient fits with the defined cluster, further measuring in the sample of oral fluid from the human patient concentrations of additional proteins IL1-β, IL6, and Collagen Telopeptide, thereby obtaining a first testing value reflecting joint concentrations of the additional proteins;

when the human patient fits with the non-defined cluster, further measuring in the sample of oral fluid of from the human patient a concentration of TIMP1, thereby obtaining a second testing value reflecting joint concentrations the TIMP1 and the earlier measured HGF;

comparing, using a processor, the first testing value or the second testing value with a threshold value reflecting in corresponding joint concentrations associated with advanced periodontitis, so as to assess whether the first testing value or the second testing value is indicative of mild periodontitis or advanced periodontitis in the human patient; and determining a treatment of the human patient based on the indication of mild periodontitis or advanced periodontitis.

14. A method comprising:
detecting a first set of proteins consisting of HGF, MMP8, and MMP9;
separately detecting a second set of proteins consisting of IL1-β, IL6, and Collagen Telopeptide;
separately detecting a third set of proteins consisting of HGF and TIMP1,
wherein detecting each of the first, second and third sets of protein comprises:
  (a) obtaining an oral fluid sample from a human patient; and
  (b) detecting whether the proteins are present in the oral fluid sample by contacting the oral fluid sample with detection reagents for binding the proteins and detecting a binding between each of the proteins and the detection reagents.

15. The system according to claim 1, wherein the biomarkers further include metallopeptidase inhibitor 1 (TIMP1), and wherein the one or more processors are configured to process the first-stage concentrations to alternatively indicate to measure, in the second stage, a concentration of TIMP1 along with the concentration of HGF.

16. The system according to claim 15, further comprising:
a first container configured to receive a portion of the sample of oral fluid sample, the first container being provided with a first detector of the at least one detector configured to measure the concentrations of HGF, MMP8, and MMP9;
a second container configured to receive another portion of the sample of oral fluid, the second container being provided with a second detector of the at least one detector configured to measure the concentrations of IL1-β, IL6, and Collagen Telopeptide; and
a third container configured to receive another portion of the sample of oral fluid, the third container being provided with a third detector of the at least one detector configured to measure the concentrations of HGF and TIMP-1.

17. The system according to claim 16, wherein the second container and the third container are separate modules, at least one which is insertable into the system.

* * * * *